Figure 3:
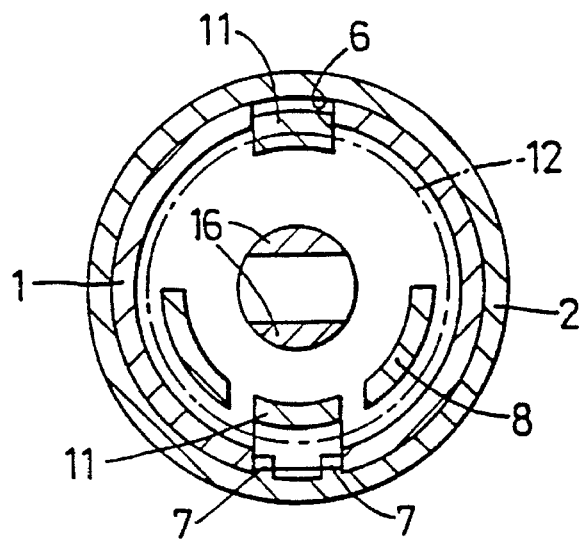

United States Patent [19]

Marshall et al.

[11] Patent Number: 5,599,309
[45] Date of Patent: Feb. 4, 1997

[54] INJECTION DEVICES

[75] Inventors: Jeremy Marshall, Jericho; David D. Crossman, Christmas Common, both of United Kingdom

[73] Assignee: Owen Mumford Limited, Oxford, United Kingdom

[21] Appl. No.: 525,700

[22] PCT Filed: Mar. 24, 1994

[86] PCT No.: PCT/GB94/00616

§ 371 Date: Sep. 25, 1995

§ 102(e) Date: Sep. 25, 1995

[87] PCT Pub. No.: WO94/21316

PCT Pub. Date: Sep. 29, 1994

[30] Foreign Application Priority Data

Mar. 24, 1993 [GB] United Kingdom .................. 9306093
Mar. 27, 1993 [GB] United Kingdom .................. 9306429

[51] Int. Cl.$^6$ ............................................ A61M 5/20
[52] U.S. Cl. .......................... 604/136; 604/134; 604/117
[58] Field of Search .................................. 604/117, 131, 604/134, 135, 136, 157; 128/760, 761, 762, 763

[56] References Cited

U.S. PATENT DOCUMENTS

| | | | |
|---|---|---|---|
| Re. 32,922 | 5/1989 | Levin et al. ........................ | 604/131 X |
| 3,712,301 | 1/1973 | Sarnoff .................................... | 604/136 |
| 5,042,977 | 8/1991 | Bechtold et al. ...................... | 604/134 |
| 5,071,353 | 12/1991 | Van Der Wal ...................... | 604/134 X |
| 5,273,544 | 12/1993 | Van Der Wal ........................ | 604/134 |
| 5,295,965 | 3/1994 | Wilmot .................................. | 604/136 |
| 5,300,030 | 4/1994 | Crossman et al. .................. | 604/134 X |
| 5,358,489 | 10/1994 | Wyrick .................................. | 604/135 X |
| 5,478,316 | 12/1995 | Bitdinger et al. .................... | 604/134 X |

FOREIGN PATENT DOCUMENTS

WO86/06966 12/1986 WIPO .................................... 604/136

*Primary Examiner*—Sam Rimell
*Attorney, Agent, or Firm*—Young & Thompson

[57] ABSTRACT

An injection device holds a syringe in the form of a capsule having a needle projecting from its forward end and a plunger extending from its rear end. The rear end of the plunger received in the drive member, which, when released, is urged forward by a coil spring, thus projecting the needle and expressing the dose. The drive member is held captive in its rearward primed position by a detent provided by the body of the device. A sleeve covering a substantial part of the body can shift longitudinally of it from an initial rearward position to a forward position in which it either disengages the drive member from the detent, or in which a trigger is freed from actuation to release the drive member.

5 Claims, 5 Drawing Sheets

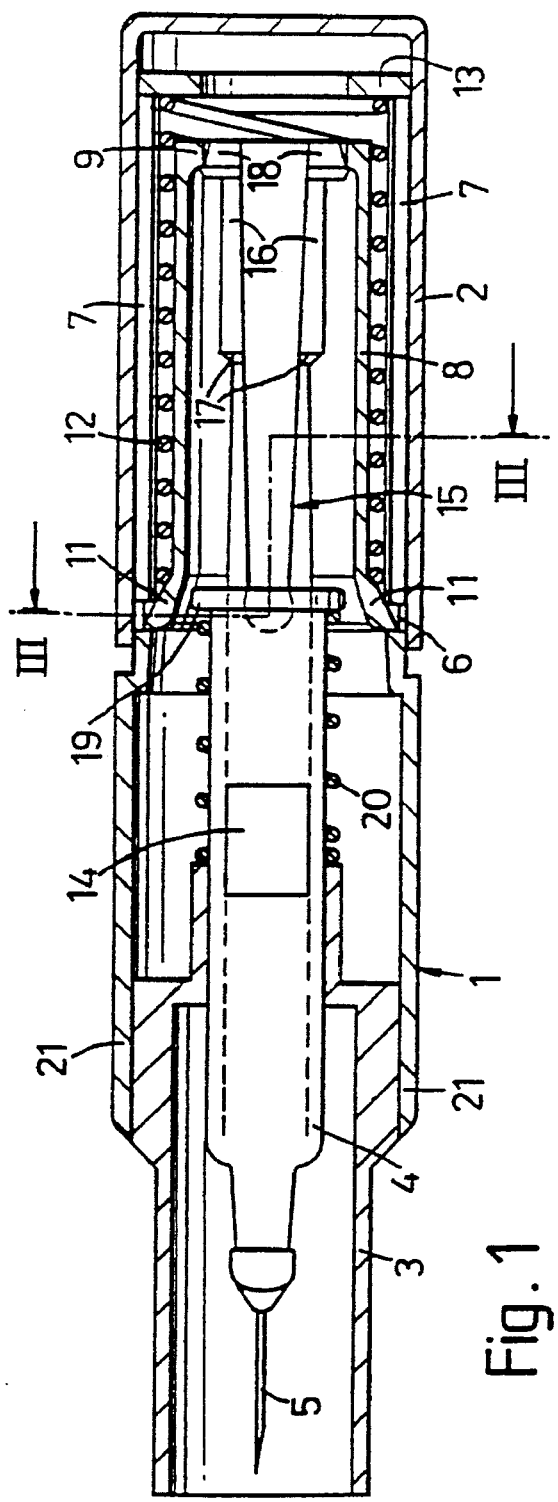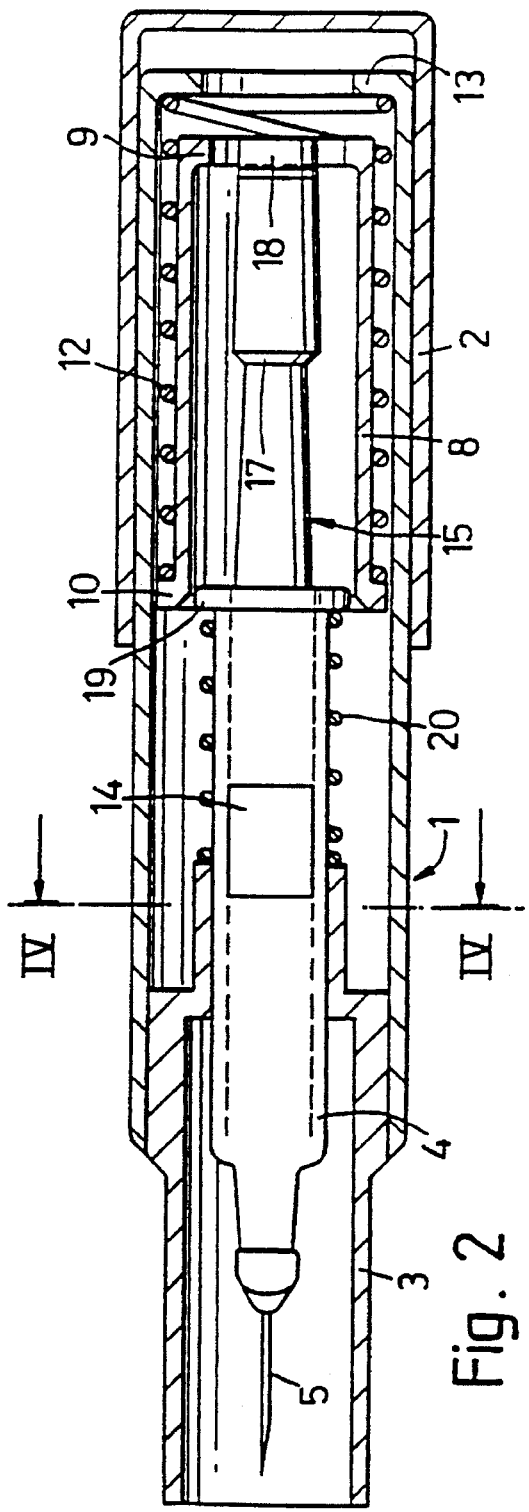

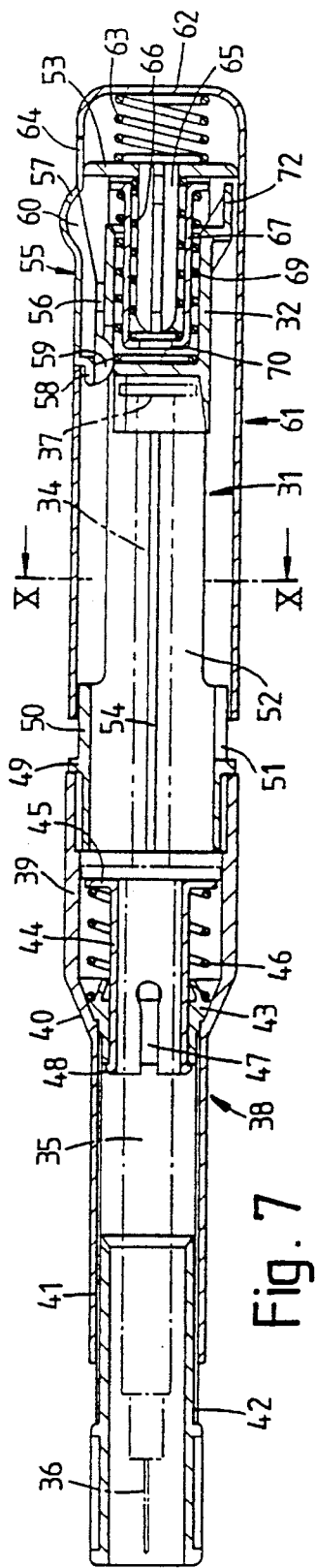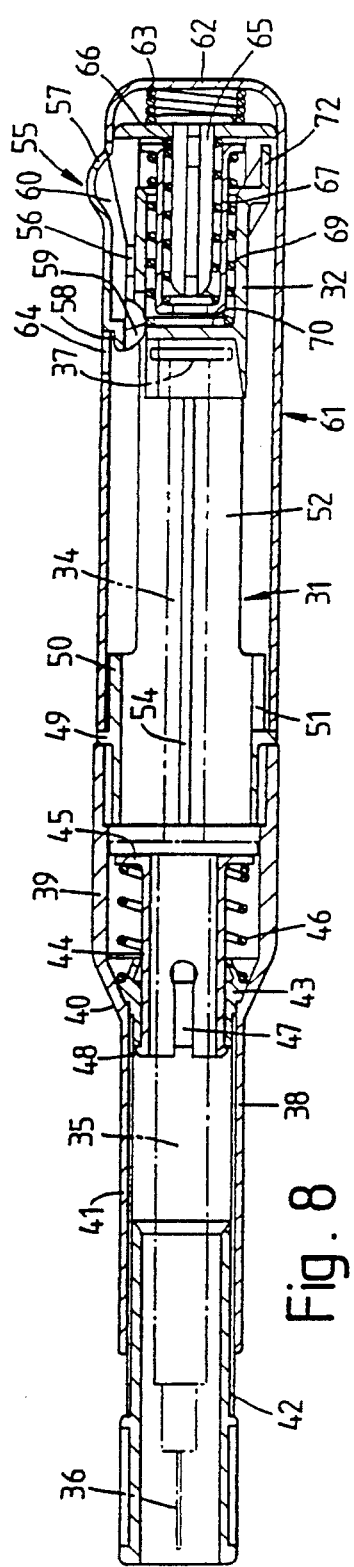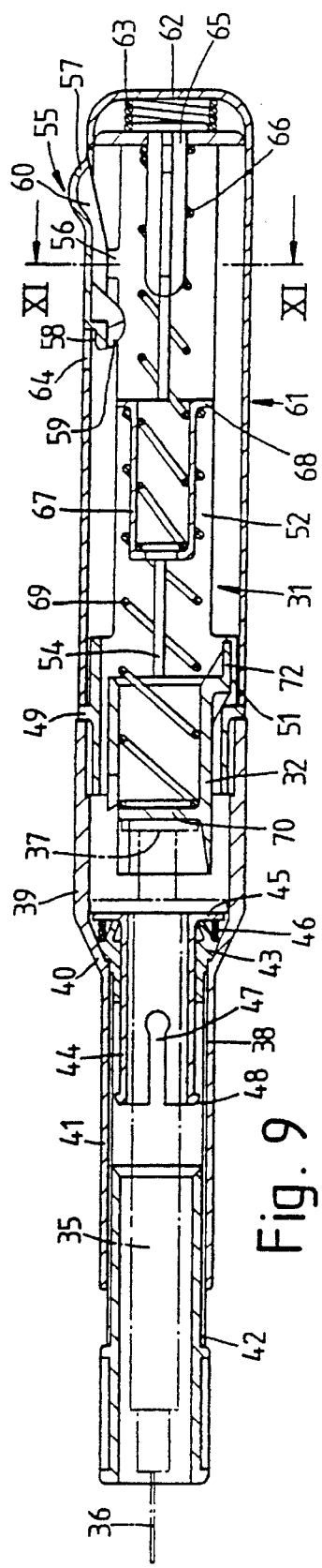

INJECTION DEVICES

This invention relates to injection devices.

In GB-B-2239180 an injection device has an elongate body of several parts which can be dismantled to insert and remove a syringe before and after use. The piston of the syringe is operated by a spring-loaded rod or plunger whose rear end is trapped by a catch, releasable by a press button. But initially this is impotent, held out of reach of the catch by an outer sleeve whose rear end it closes, the sleeve and button being lightly urged to the rear by a spring. For an injection, the device can be held by this sleeve and when the forward end is pressed against the skin, the sleeve moves forwards, bringing the button in range of the catch. Pressing the button then releases the plunger and the injection is carried out, the first part of the plunger stroke projecting the needle by shifting the syringe and the second part ejecting the fluid charge of the syringe through the needle. The arrangement gives a certain security against inadvertent actuation, and makes self-administration of an injection more reliable.

However, there are some drawbacks with this device. In particular, the plunger has to be specially formed first to have an effective engagement by the catch and secondly to provide an abutment for the coil compression spring which drives it. The part of the plunger which engages the catch of course has to be at the rear end, which means that the coil spring has to begin forward of the catch, so as not to interfere. Since the coil spring has to be quite long even when compressed (to be able to extend over both parts of the plunger stroke while maintaining its pressure on the syringe piston) the abutment on the plunger must be a good distance from the rear end. It also has to be a good distance from the syringe, to allow sufficient travel for the plunger. The arrangement leads to a device which is about three times as long as the syringe body.

Another snag is that a syringe with its own plunger already fitted and not removable is not usable in the device.

It is the aim of this invention to provide an injection device which, while having most of the benefits of GB-B-2239180, can be considerably more compact and be usable with syringes having their own plungers.

According to the present invention there is provided an injection device in which a charged capsule with a needle at its forward end and a plunger projecting from its rear end is housed in an elongate body with coil spring means which, when released from compression, act on the plunger to push that forwards and thereby carry out the injection, and a release mechanism for the spring means including a sleeve over a substantial part of the body initially retained in or urged into a rearward position but which has to be shifted forwards in relation to the body to allow the spring means to be released, characterised in that the spring means act between the rear end of the body and a drive member that receives the rear end of the plunger, and in that the release mechanism includes a detent, provided by the body, that engages the drive member adjacent its forward end.

In one form, the release mechanism includes an outwardly projecting formation on the drive member that initially engages the detent, the sleeve being arranged when shifted forwards, to engage said formation and press it inwards releasing it from the detent.

Conveniently, the drive member will be generally cylindrical and surrounded by the coil spring means which act against an abutment adjacent the forward end of said drive member. The rear end of the drive member will be at least partially closed to engage the rear end of the plunger.

The forward end of the device may have a removable cap which, when properly fitted on the body, is abutted by the sleeve, the sleeve thereby being prevented by moving forwards to allow release of the spring means.

In another form, the release mechanism includes a trigger, carried by said body, which initially engages the drive member, the trigger being accessible through an aperture in said sleeve, being held inoperable by the sleeve when that is to the rear, and being actuable to release the drive member when the sleeve has been shifted forwards. Conveniently, the trigger has a pivoting action, being pressed in at the rear to lift the forward end clear of the drive member, said forward end being trapped by sleeve when that is at its rearward position but coming clear into said aperture when the sleeve is shifted forwards.

The drive member may be generally cylindrical and open ended, but with an intermediate transverse wall forming a forward facing cup to receive the rear end of the plunger and a rearward facing cup to receive the coil spring means.

The coil spring means may comprise two coil springs of different diameter and an intermediate generally cylindrical member which initially telescope together with said drive member, one spring acting between the rear end of the body and an abutment at the forward end of the intermediate member, and the other spring acting between an abutment at the rear end of the intermediate member and said transverse wall.

The body and the drive member may have co-operating formations to guide the drive member when released.

Figure 4:
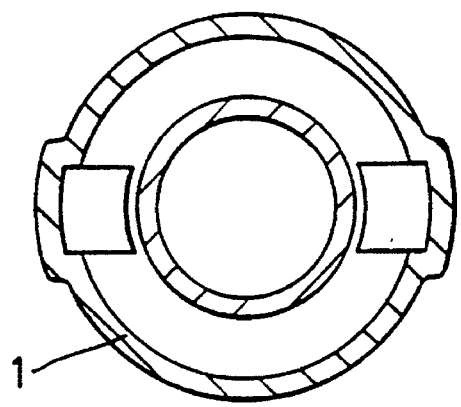
Figure 5:
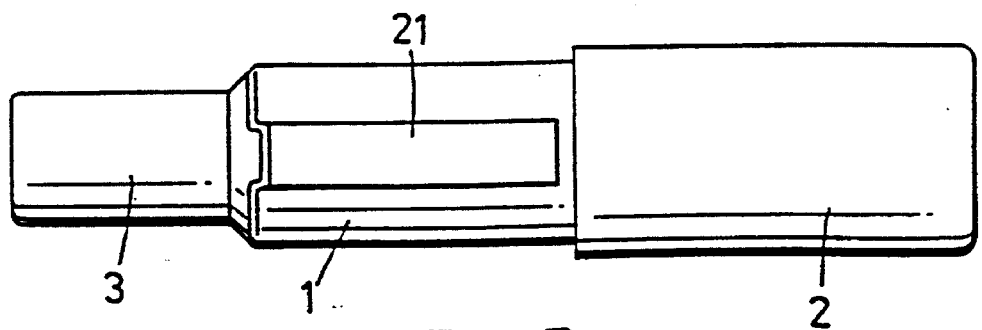
Figure 6:
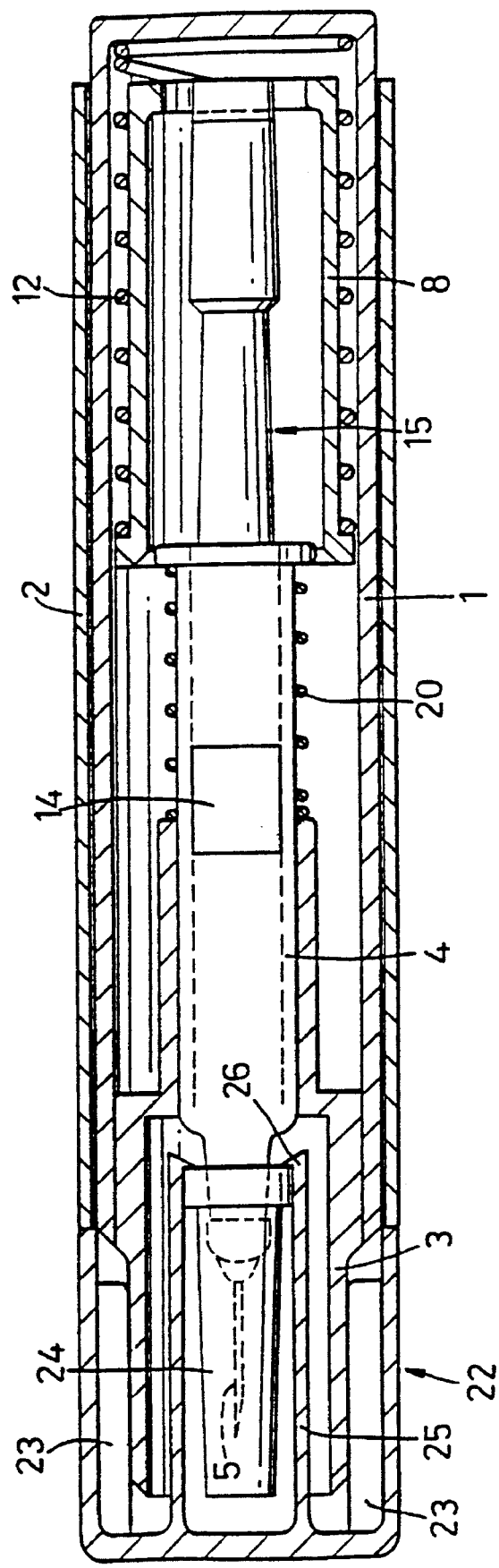
Figure 10:
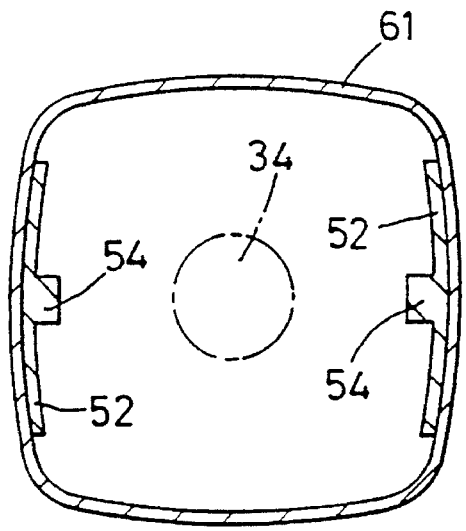
Figure 11:
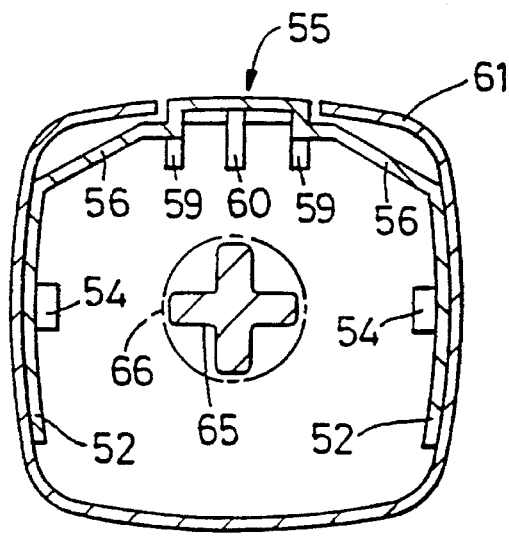
Figure 12:
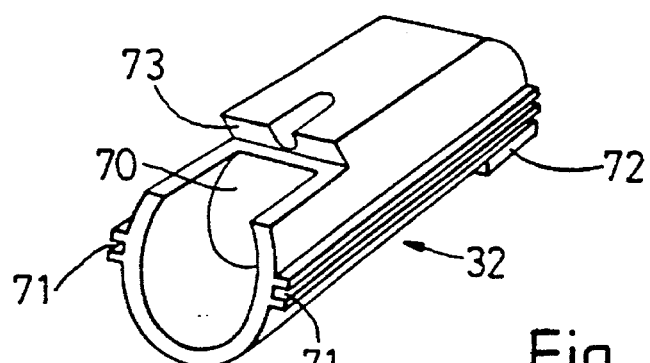

For a better understanding of the invention, some embodiments will now be described, by way of example, with reference to the accompanying drawings, in which:

FIG. 1 is an axial section of an injection device,

FIG. 2 is another axial section of that device, at right angles to the view of FIG. 1, FIG. 3 is a cross section on the line III—III of FIG. 1, FIG. 4 is a cross section on the line IV—IV of FIG. 2, FIG. 5 is a side view of the injection device, FIG. 6 is an axial section of an alternative injection device, FIG. 7 is an axial section of a further injection device in an out of use condition, FIG. 8 is an axial section of the device of FIG. 7 when primed ready for use, FIG. 9 is an axial section of the device of FIG. 7 after use, FIG. 10 is a cross section, to a larger scale, on the line X—X of FIG. 7, FIG. 11 is a cross section, to a larger scale, on the line XI—XI of FIG. 9, and FIG. 12 is a perspective view of a drive member forming part of the injection device of FIG. 7.

The device of FIGS. 1 to 5 has a generally cylindrical barrel 1 over the rear end portion of which is sleeved an elongate cylindrical cap 2. At the forward end, a nose piece 3 is fitted into the mouth of the barrel 1 and provides a shield and a guide for a capsule 4 with a needle 5.

The rear portion of the barrel i has two diametrically opposed axially extending slots 6 and the rear end cap 2 has corresponding pairs of opposed internal ribs 7 engaged in these slots, which act as guides and allow limited relative axial movement between the barrel 1 and the end cap 2. The end cap has sufficient resilience to be forced over the rear end of the barrel until the ribs 7 snap into the slots 6.

Within the rear portion of the barrel 1 there is a drive member in the form of a co-axial cylinder 8 with an inturned rim 9 at its rear end and an out-turned rim 10 around most of its forward end. But this is interrupted by two diametrically opposite, integrally formed resilient tongues 11 which project further forwardly and outwardly, where they normally abut the forward ends of the slots 6. The rear sides of these tongues are sloped and are engaged by the forward ends of the ribs 7.

A coil spring 12 encircles the cylinder 8 and acts between an inturned flange 13 at the rear end of the barrel 1 and the out-turned rim 10 of the cylinder 8. The capsule 4 has a piston 14 operated by a plunger 15 which is driven by the spring 12 acting through the cylinder 8. The plunger is bifurcated into two fingers 16 over its rear portion and these step outwardly at shoulders 17 at about their mid length and terminate at stepped and tapered formations 18. These are engaged, as can been seen in FIG. 1, by the inturned rim 9, but the fingers 16 are capable of being squeezed together, in which case the formations 8 and the rest of the plunger can pass freely through the rear end of the cylinder 8.

The capsule 4 has an out-turned flange 19 at its rear end and a coil spring 20 surrounding the capsule acts between this and the rear of the nose 3. This spring 20 is substantially weaker than the spring 12.

Finally, the forward part of the barrel 1 is not truly cylindrical but is formed with two diametrically opposed outwardly projecting ribs 21 aligned with the slots 6.

Initially, the device is as shown in FIGS. 1 and 2. The needle 5 is just within the forward end of the nose 3, and thus safe. The device is applied against the patient's skin and the rear end cap 2 is pressed forwardly, its movement being limited by abutment with the rear ends of the ribs 21. The forward ends of the ribs 7 wedge the tongues 11 inwards until they clear the detents formed by the forward ends of the slots 6. The coil spring 12 is now free to act and shoots the cylinder 8 forwards, easily overcoming the relatively weak spring 20. The capsule 4 is shifted forwards by this, the plunger 15 acting through the piston 14 and the effectively solid liquid charge in the capsule. The needle 5 thus penetrates the flesh which, due to the pressure exerted on the device, bulges smoothly into the nose piece 3. Such penetration is therefore automatically the maximum amount possible. When the spring 20 is fully compressed the capsule 4 is arrested, but the spring 12 continues to act, squeezing liquid out of the capsule 4 through the needle 5. When the shoulders 17 reach the flange 19, the fingers 16 are pinched in and the formations 18 are released from the rim 9. The plunger 15 is thereby disengaged from the drive member 8, and so the spring 20 can now assert itself and return the capsule 4 to its initial position.

This automatic retraction is preferred, but it does require the plunger 15 to be in a particular form. The device could work in non-retractive manner with a proprietary syringe having a plain plunger, provided the inturned rim 9 reduced the aperture to less than the size of the rear end head.

The device of FIG. 6 is similar in many respects. However it is designed to avoid accidental actuation, which is possible with the device described above. Here, there is an end cap 22 which can close the forward end of the barrel 1 by shrouding the nose 3. It has internal ribs 23 which co-axially locate it by bearing on the projecting portion of the nose. The member 2 is extended forwardly and abuts the forward end cap 22 when that is properly fitted. This makes the barrel 1 virtually inaccessible, although the member 2 here is basically a sleeve and is not closed over the rear end of the barrel 1. But in any event the sleeve 2 cannot be shifted forward with respect to the barrel, at least not until the cap 22 is removed, which is done only just before injection.

It is common for the needle 5 to be encased in a rubber or plastics sheath 24, whose base encircles the neck of the capsule. This is not easy to remove if largely concealed within the nose 3. However, the cap 22 provides means for removing this sheath in the form of an inner cylindrical projection 25 with an inturned rim 26 at the rear end which snaps behind the base of the sheath 24 when the cap is properly fitted. When the cap 22 is removed, the sheath 24 is simultaneously plucked off the capsule.

The injection device of FIGS. 7 to 12 has an elongate body 31, as described in more detail below, which carries and guides a generally cylindrical drive member 32 urged forwardly (to the left in the figures) by a spring assembly, also to be described in more detail later. The drive member 32 co-operates with a plunger 34 of a capsule 35 with a forwardly projecting needle 36. These parts 34, 35 and 36 comprise a proprietary syringe, and are shown in chain dotted lines. Initially, the plunger 34 is extended to the rear and its head 37 is received in a forward facing cup formed by the front end of the drive member 32.

A barrel 38 is screwed co-axially onto the forward end of the body 31 by its larger cylindrical portion 39. Forward of this it reduces at a sloping shoulder 40 and then continues in a smaller cylindrical portion 41. A nose 42 screws into the forward end of this portion 41 and serves as a shield for the needle 36 and as means for adjusting the depth of injection.

Internally, the barrel 38 receives a collar 43 which locates against the shoulder 40 and guides a tube 44 with an outwardly projecting flange 45 at its rear end. A light coil spring 46, much weaker than the spring assembly for the drive member 32, encircles this tube and acts between the collar 43 and flange 45. A certain resilience is given to the forward end of the tube by longitudinal cut outs 47, which enable a tooth-sectioned outer rim 48 to snap past the collar and retain the tube. The capsule 35 passes through this tube 44 and its rear end flange locates against the flange 45.

When fully screwed home onto the body 31, the barrel 38 abuts a circumferential rib 49. To the rear of this, the body 31 becomes a substantially square formation 50, but with rounded corners, and one of the sides of the square has a slot 51 open to the rear. Over most of its length, the body 31 then comprises two spaced, parallel side walls 52 extending from the sides of the formation 50 flanking the slot 51 to a rear end plate 53 with a rounded square periphery matching the formation 50. Along the inner sides of these walls 52, as best seen in FIG. 10, there are longitudinal ribs 54.

Towards the rear end, the body is also formed with an integral trigger 55 aligned with the length of the body 31. This is carried by symmetrical bridge pieces 56 sloping up towards each other from the top edges of the walls 52 and slim enough and/or weakened enough to allow the trigger 55 to pivot at about its mid-point. To the rear, the trigger has a rounded thumb or finger pad 57, while towards the front it has a downward step 58 in its upper surface and underneath that hooks 59. The trigger is made rigid in itself by the provision of ribs 60 extending longitudinally of its underside.

The body 31 is largely encased by a sleeve 61 closed at its rear end 62. The forward end of the sleeve can slide over the formation 50, and the rear end is a sliding fit over the plate 53. Initially it is lightly urged to the rear by a coil spring 63 acting between the plate 53 and the end 62. The trigger 55 is exposed through a rectangular aperture 64, and is initially substantially flush with the sleeve 61, but with its step 58 engaged under the forward edge of the aperture 64. This means that the pad 57 cannot be pressed inwards to any significant degree. In this position, the hooks 59 engage the drive member 32 and hold it to the rear.

Ideally, a single coil spring would be used to drive the member 32. However, it requires a considerable travel, and while a single spring has been found to work well enough with the previous embodiments without a trigger, it has been found less satisfactory in this embodiment. There is a tendency for the spring to buckle when fully compressed and become entangled with the trigger. Therefore, the drive is preferably achieved by two coil springs of different diameter working in concert.

The rear end plate 53 of the body 31 is centrally apertured to receive a spigot member 65 which projects forwardly, co-axial with the body 31. It locates a first drive spring 66, which acts between the end plate 53 and the base of an elongated cup 67 in which initially it is largely housed. This cup has an outwardly projecting flange 68 at its rear, open end, and the second drive spring 69 acts between this and a wall 70 across the cylindrical drive member 32. The other side of this wall 70 forms the base of the cup which receives the plunger head 37. Initially, the spring 69 is largely housed within the drive member 32 and confined between its cylindrical wall and the outside of the cup 67.

The drive member 32 is guided and held against rotation by grooves 71 (FIG. 12) on opposite sides which are engaged by the ribs 54. There is sufficient flexibility in the plastics moulding of the body 31 to allow the two parts to be snapped together. The cup 67 can likewise be guided and held against rotation by the ribs 54 co-operating with its flange 68.

On the side opposite the trigger 55, the drive member 32 is stepped outwardly at its rear end to provide an abutment 72, which is aligned with the slot 51. Also, the forward part of the drive member 32 initially just below the trigger is shaped to make an undercut shoulder 73 that will be positively engaged by the hooks 59.

Initially, the device is as shown in FIG. 7, with the drive member 32 to the rear and the springs 66 and 69 fully compressed. The sleeve 61 is to the rear holding the trigger 55 safe.

The depth of needle penetration is adjusted by screwing out the nose 42. The more it is screwed out, the shallower the injection will be. The outer circumference of the nose can be given markings to indicate the depth against the forward end of the barrel 38.

The device is primed by sliding the sleeve 51 forwards until it abuts the rib 49, as shown in FIG. 8. This brings the trigger 55 clear within the compass of the aperture 64. If the user is not quite ready, he can release the sleeve and the spring 63 will push it back to make the trigger safe again.

Normally the user will press the nose 42 against the place where the injection is to be made holding the sleeve 61 by one hand. This will automatically prime the device. Then, the freed trigger 53 is pressed, releasing the drive member 32, This shoots forward, acting on the plunger 34. The virtually solid liquid in the capsule 35 and the very fine escape route through the needle 36 causes the capsule to be carried forward until the spring 46 is fully compressed. With the capsule 35 able to go no further, the plunger 34 is urged forward relative to it, squeezing out the dose though the needle 36 which is now at its set penetration. The injection ends with the various parts as shown in FIG. 9, the drive member 32 being adjacent the capsule 35 with the abutment 72 in the slot 51 and the cup 67 being at about the mid-length of the body 31.

Provision can be made for automatic disengagement at this point of the plunger 34 and the drive member 32, so that the spring 46 can exert itself and carry the capsule back again, thereby withdrawing the needle 36 to a safe position, as with the previous embodiments.

Also, the devices of FIGS. 1 to 6 could have the double spring and drive member guiding arrangements similar to those just described.

We claim:

1. An injection device comprising an elongate body in which is housed a charged capsule with a needle at the forward end of the capsule and a plunger projecting from the rear end of the capsule, coil spring means arranged between the rear end of the body and a drive member that receives the rear end of the plunger and which spring means, when released from compression, act through the drive member on the plunger to push the plunger forwards and thereby carry out an injection, and a release mechanism for the drive member including a sleeve over part of the body and slidable longitudinally thereof between rearward and forward positions, and a trigger carried by said body and accessible through an aperture in said sleeve, the sleeve being initially in said rearward position where it holds the trigger inoperable and in retaining engagement with the drive member but which when shifted to said forward position allows the trigger to be actuated and thus the drive member to be released.

2. An injection device as claimed in claim 1, wherein the trigger has an intermediate pivotal connection to the body whereby, when the trigger is pushed in at the rear, the forward end of the trigger is lifted clear of the drive member, said forward end being trapped by the sleeve when the sleeve is at its rearward position but coming clear into said aperture when the sleeve is shifted forwards.

3. An injection device as claimed in claim 1, wherein the drive member is generally cylindrical and open ended, but with an intermediate transverse wall forming a forward facing cup to receive the rear end of the plunger and a rearward facing cup to receive the coil spring means.

4. An injection device as claimed in claim 1, wherein the coil spring means comprises two coil springs of different diameter and an intermediate generally cylindrical member which initially telescope together with said drive member, one spring acting between the rear end of the body and an abutment at the forward end of the intermediate member, and the other spring acting between the rear end of the intermediate member and said transverse wall.

5. An injection device as claimed in claim 1, wherein said body and the drive member have mutually engaging formations extending in the longitudinal direction of the body to guide the drive member when released.

* * * * *